US012629821B2

(12) United States Patent
Barral et al.

(10) Patent No.: US 12,629,821 B2
(45) Date of Patent: *May 19, 2026

(54) SYSTEMS AND METHODS FOR PREVENTION OF SURGICAL MISTAKES

(71) Applicant: Verily Life Sciences LLC, South San Francisco, CA (US)

(72) Inventors: Joëlle Barral, Mountain View, CA (US); Martin Habbecke, Palo Alto, CA (US); Daniele Piponi, Oakland, CA (US); Thomas Teisseyre, Pacifica, CA (US)

(73) Assignee: Verily Life Sciences LLC, Dallas, TX (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/850,765

(22) Filed: Jun. 27, 2022

(65) Prior Publication Data

US 2022/0324102 A1 Oct. 13, 2022

Related U.S. Application Data

(63) Continuation of application No. 15/686,840, filed on Aug. 25, 2017, now Pat. No. 11,370,113.

(Continued)

(51) Int. Cl.
*G06N 20/00* (2019.01)
*A61B 34/00* (2016.01)
(Continued)

(52) U.S. Cl.
CPC .............. *B25J 9/163* (2013.01); *A61B 34/25* (2016.02); *A61B 34/30* (2016.02); *G05B 13/028* (2013.01);
(Continued)

(58) Field of Classification Search
CPC .......... B25J 9/163; A61B 34/25; A61B 34/30; A61B 2034/254; A61B 34/32;
(Continued)

(56) References Cited

U.S. PATENT DOCUMENTS 5,791,907 A    8/1998   Ramshaw et al.
7,966,269 B2   6/2011   Bauer et al.
(Continued)

FOREIGN PATENT DOCUMENTS

CN    101821743 A    9/2010
CN    104914726 A    9/2015
(Continued)

OTHER PUBLICATIONS

Office Action mailed Oct. 21, 2022, in corresponding Chinese application No. 201780054318.X (Chinese version), 7 pages.
(Continued)

*Primary Examiner* — Casey R. Garner
(74) *Attorney, Agent, or Firm* — Christensen O'Connor Johnson Kindness PLLC

(57) ABSTRACT

An apparatus, system and process for guiding a surgeon during a medical procedure to prevent surgical mistakes are described. The system may include a machine learning medical procedure server that generates one or more machine learning medical procedure models using, at least, medical procedure data captured during medical procedures performed at a plurality of different medical procedure systems. The system may also include a medical procedure system communicably coupled with the machine learning medical procedure server that receives a selected machine learning medical procedure model from the machine learning medical procedure server, and utilizes the selected machine learning medical procedure model during a corre-
(Continued)

sponding medical procedure to control one or more operations of the medical procedure system.

20 Claims, 7 Drawing Sheets

Related U.S. Application Data

(60) Provisional application No. 62/383,838, filed on Sep. 6, 2016.

(51) Int. Cl.

| | |
|---|---|
| *A61B 34/30* | (2016.01) |
| *B25J 9/16* | (2006.01) |
| *G05B 13/02* | (2006.01) |
| *G05B 13/04* | (2006.01) |
| *G16H 40/63* | (2018.01) |
| *G16H 50/20* | (2018.01) |
| *G16H 50/50* | (2018.01) |
| *G16H 50/70* | (2018.01) |
| *A61B 34/32* | (2016.01) |
| *A61B 34/37* | (2016.01) |

(52) U.S. Cl.
CPC ............. *G05B 13/04* (2013.01); *G06N 20/00* (2019.01); *G16H 40/63* (2018.01); *G16H 50/20* (2018.01); *G16H 50/50* (2018.01); *G16H 50/70* (2018.01); *A61B 2034/254* (2016.02); *A61B 34/32* (2016.02); *A61B 34/37* (2016.02)

(58) Field of Classification Search
CPC ........ A61B 34/37; G16H 50/50; G16H 50/70; G16H 50/20; G16H 40/63; G06N 20/00; G05B 13/028; G05B 13/04
See application file for complete search history.

(56) References Cited

U.S. PATENT DOCUMENTS

| | | | |
|---|---|---|---|
| 8,560,047 | B2 | 10/2013 | Haider et al. |
| 9,129,054 | B2 | 9/2015 | Nawana et al. |
| 2007/0270685 | A1 | 11/2007 | Kang et al. |
| 2011/0166703 | A1* | 7/2011 | Byrne et al. |
| 2013/0331730 | A1* | 12/2013 | Fenech et al. |
| 2014/0142591 | A1 | 5/2014 | Alvarez et al. |
| 2015/0306763 | A1 | 10/2015 | Meier et al. |
| 2015/0332196 | A1* | 11/2015 | Stiller et al. |
| 2016/0228204 | A1* | 8/2016 | Quaid et al. |
| 2016/0331474 | A1 | 11/2016 | Lacal et al. |
| 2017/0084036 | A1 | 3/2017 | Pheiffer et al. |
| 2017/0165013 | A1* | 6/2017 | Itkowitz ................. A61B 90/37 |
| 2017/0334066 | A1* | 11/2017 | Levine ................... G06N 3/045 |
| 2019/0333638 | A1 | 10/2019 | Elidan et al. |

FOREIGN PATENT DOCUMENTS

| | | |
|---|---|---|
| CN | 105144171 A | 12/2015 |
| ES | 2 534 140 B1 | 3/2016 |
| WO | 2017151904 A1 | 9/2017 |
| WO | WO-2017216645 A2 * | 12/2017 |

OTHER PUBLICATIONS

Communication Pursuant to Article 94(3) EPC mailed Jul. 15, 2020, issued in European Application No. 17767971.9, filed Sep. 1, 2017, 12 pages.

PCT/US2017/049971, International Search Report and Written Opinion of the International Searching Authority, mailed Dec. 7, 2017, 16 pages.

Notice of Reasons for Rejection mailed Feb. 26, 2020, issued in corresponding Japanese Application No. 2019-510306, filed Sep. 1, 2017, 11 pages.

Chui, Chee-Kong, Binh P. Nguyen, and Rong Wen. "Development of a cognitive engine for balancing automation and human control of surgical robotic system." In 2014 11th International Conference on Ubiquitous Robots and Ambient Intelligence (U RAI), pp. 13-17. IEEE, 2014. (Year: 2014).

Berthet-Rayne, Pierre, Maura Power, Hawkeye King, and Guang-Zhong Yang. "Hubot: A three state Human-Robot collaborative framework for bimanual surgical tasks based on learned models." In 2016 IEEE International Conference on Robotics and Automation (ICRA), May 16, 2016 (pp. 715-722). IEEE. (Year: 2016).

Lin, Henry C., Izhak Shafran, David Yuh, and Gregory D. Hager. "Towards automatic skill evaluation: Detection and segmentation of robot-assisted surgical motions." Computer Aided Surgery 11, No. 5 (2006): 220-230. (Year: 2006).

Extended European Search Report mailed Jun. 15, 2022, issued in corresponding European Application No. EP 21 21 4576 filed Sep. 1, 2017, 9 pages.

* cited by examiner

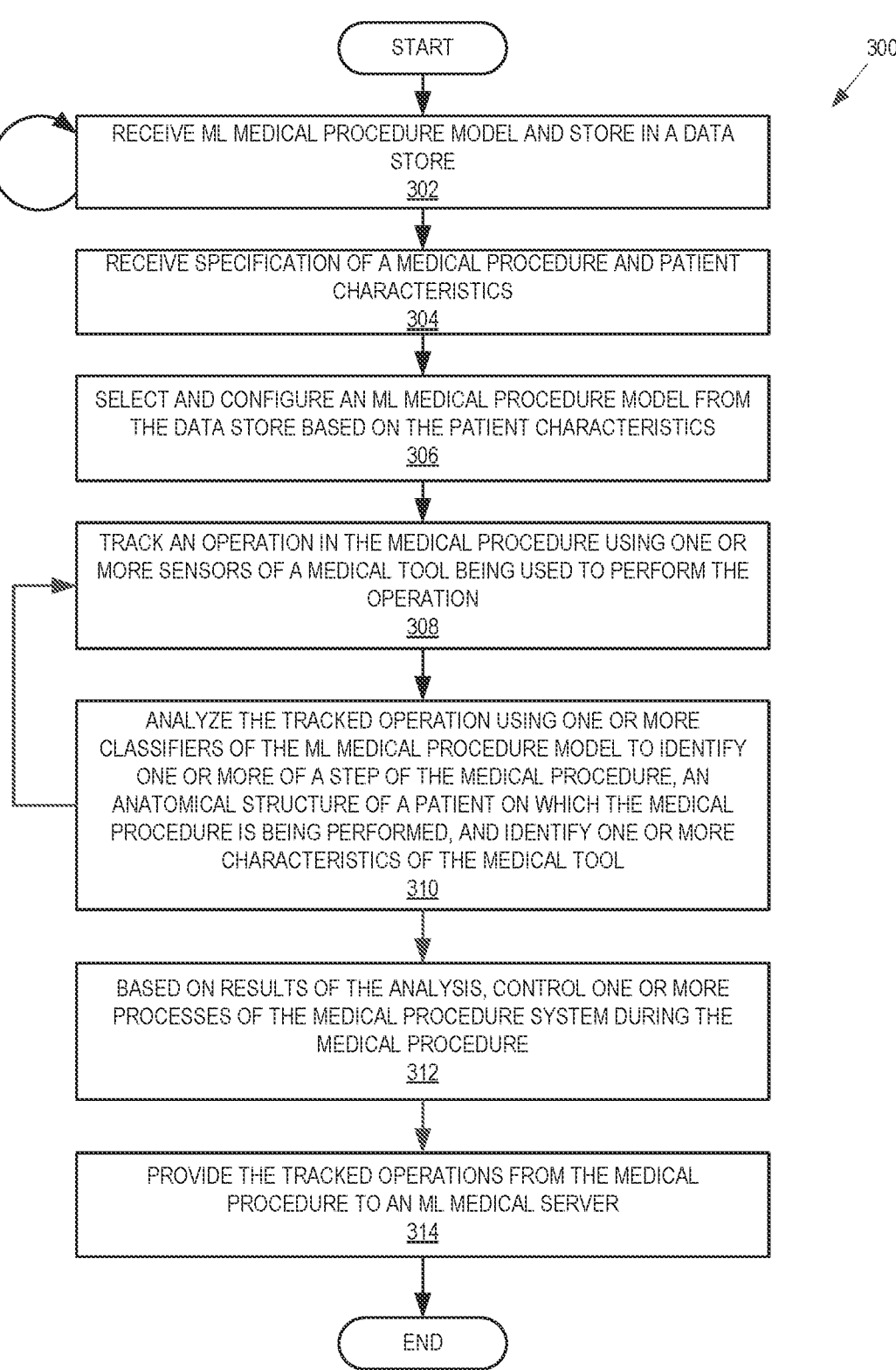

300

START

RECEIVE ML MEDICAL PROCEDURE MODEL AND STORE IN A DATA
STORE
302

RECEIVE SPECIFICATION OF A MEDICAL PROCEDURE AND PATIENT
CHARACTERISTICS
304

SELECT AND CONFIGURE AN ML MEDICAL PROCEDURE MODEL FROM
THE DATA STORE BASED ON THE PATIENT CHARACTERISTICS
306

TRACK AN OPERATION IN THE MEDICAL PROCEDURE USING ONE OR
MORE SENSORS OF A MEDICAL TOOL BEING USED TO PERFORM THE
OPERATION
308

ANALYZE THE TRACKED OPERATION USING ONE OR MORE
CLASSIFIERS OF THE ML MEDICAL PROCEDURE MODEL TO IDENTIFY
ONE OR MORE OF A STEP OF THE MEDICAL PROCEDURE, AN
ANATOMICAL STRUCTURE OF A PATIENT ON WHICH THE MEDICAL
PROCEDURE IS BEING PERFORMED, AND IDENTIFY ONE OR MORE
CHARACTERISTICS OF THE MEDICAL TOOL
310

BASED ON RESULTS OF THE ANALYSIS, CONTROL ONE OR MORE
PROCESSES OF THE MEDICAL PROCEDURE SYSTEM DURING THE
MEDICAL PROCEDURE
312

PROVIDE THE TRACKED OPERATIONS FROM THE MEDICAL
PROCEDURE TO AN ML MEDICAL SERVER
314

END

FIG. 3

SYSTEMS AND METHODS FOR PREVENTION OF SURGICAL MISTAKES

CROSS-REFERENCE TO RELATED APPLICATION

This application is a continuation of U.S. patent application Ser. No. 15/686,840, filed Aug. 25, 2017, which claims the benefit of U.S. Provisional Application No. 62/383,838 filed on Sep. 6, 2016, the entire contents of which are incorporated herein by reference for all purposes.

TECHNICAL FIELD

This disclosure relates generally to surgical systems for medical treatment, and in particular but not exclusively, to the systems and methods for guiding a surgeon during a medical procedure to prevent surgical mistakes.

BACKGROUND INFORMATION

A significant number of complications in surgery result from a surgeon making a wrong decision during a surgical procedure. The two main causes for wrong decisions are misidentification of important anatomical structures (e.g., cutting a neurovascular bundle because it was not identified as such) and disobeying required preconditions (e.g., cutting before placing all necessary clips). Furthermore, surgical steps can be performed in the wrong order due to the lack of experience of a particular medical professional. Other mistakes may also be made during a surgical procedure.

These problems may be exacerbated when a medical professional performs minimally invasive surgery (MIS) and/or robotically assisted surgery. For example, misidentification of anatomical structures is more likely to occur in MIS and/or robotic procedures due to a surgeon's very limited endoscopic field of view of a patient's anatomical structures, as well as due to the lack of haptic feedback.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIG. 3 is a flowchart illustrating a process for providing guidance and support with a medical procedure system, in accordance with an embodiment of the disclosure.

DETAILED DESCRIPTION

Figure 1:
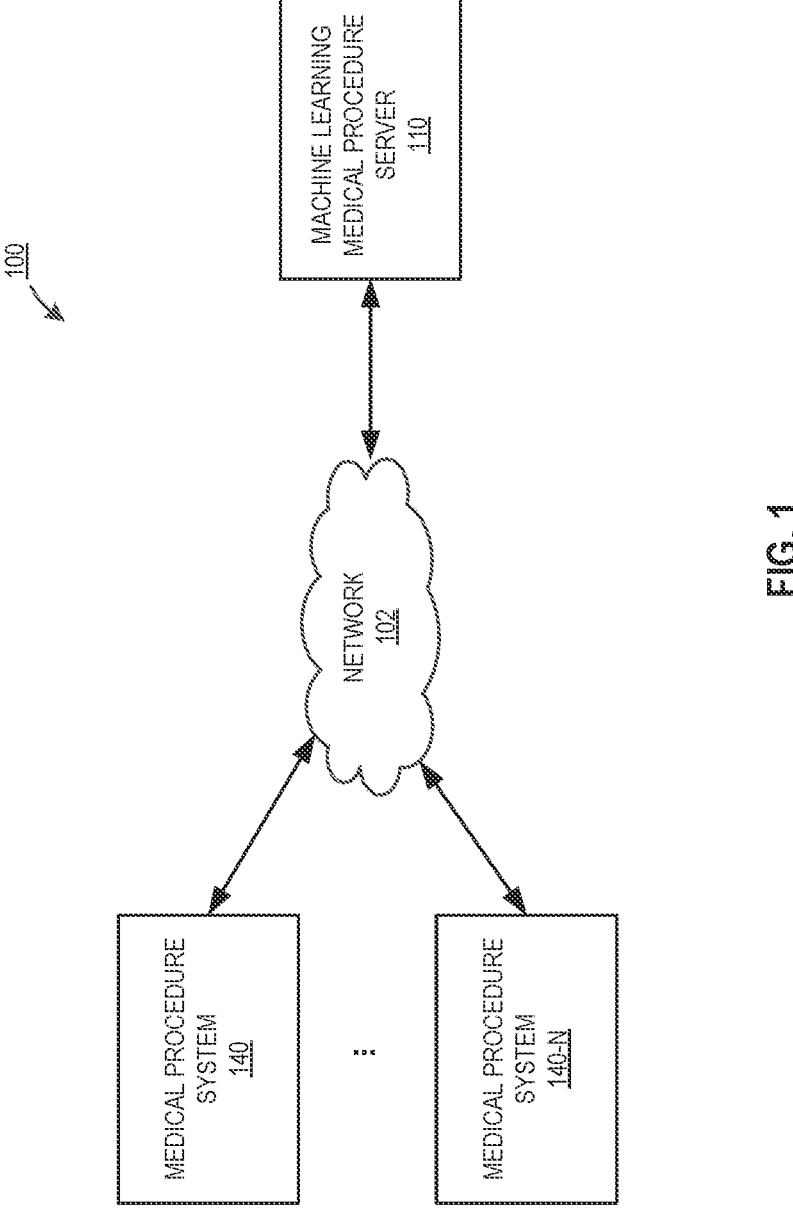
FIG. 1 is a block diagram of an exemplary system architecture 100 for preventing medical mistakes during surgical procedures by providing machine learning model based guidance and support with a medical procedure system.

Embodiments of an apparatus, system, and process for generating machine learning based models from medical procedures, which enable medical procedure systems to provide support and/or guidance to medical professionals during medical procedures, are described herein. In the following description, numerous details are set forth. It will be apparent, however, to one of ordinary skill in the art having the benefit of this disclosure, that the present invention may be practiced without these specific details. In some instances, well-known structures and devices are shown in block diagram form, rather than in detail, in order to avoid obscuring the present invention.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "generating", "receiving", "controlling", "preventing", "tracking", "enabling", "providing", "pushing", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

FIG. 1 is a block diagram of an exemplary system architecture 100 for preventing medical mistakes during surgical procedures by providing machine learning model based guidance and support with a medical procedure system. In one embodiment, the system includes a machine learning (ML) medical procedure server 110 and one or more medical procedure systems (e.g., medical procedure system 140 through medical procedure system 140-N). In one embodiment, medical procedure systems 140 through 140-N may each be a computer processing system, such as a personal computer, purpose built computing system, computing appliance, etc. The ML medical procedure server 110 may also be a computing system, such as one or more server computers, desktop computers, etc.

The medical procedure systems 140 through 140-N and the ML medical procedure server 110 may be coupled to a network 102 that communicates using any of the standard protocols for the exchange of information. In one embodiment, the medical procedure systems are coupled with network 102 via a wireless connection, such as a wireless fidelity connection, etc. The medical procedure systems 140 through 140-N and the ML medical procedure server 110 may run on one Local Area Network (LAN) and may be incorporated into the same physical or logical system, or different physical or logical systems. Alternatively, the medical procedure systems 140 through 140-N and the ML medical procedure server 110 may each reside on different LANs, wide area networks, cellular communication networks, etc. that may be coupled together via the Internet but separated by firewalls, routers, and/or other network devices. It should be noted that various other network configurations can be used including, for example, hosted configurations, distributed configurations, centralized configurations, etc.

The medical procedure systems 140 through 140-N are responsible for providing guidance and support to medical professionals during surgical procedures. In embodiments, as discussed in greater detail below, each medical procedure system can be coupled with one or more medical tools, such as stereoscopic endoscopes, robotically controlled medical instruments (e.g., calipers, spreaders, cutters, etc.). Each medical procedure system may also be coupled with one or more user interfaces, such as graphical user interfaces that display data gathered by the medical tools (e.g., a field of view of a patient's anatomical structure captured by an endoscope), provide haptic feedback (e.g., activate a visual, auditory, or sensory alarm), enable access to additional data (e.g., preoperative medical images, a patient's medical history, a patient vital information, etc.), provide additional visualizations (e.g., such as a table the patient is on, arms of robotic surgical equipment, etc.), as well as other interfaces. In embodiments, each medical procedure system may have different sets of medical tools and user interfaces based on the desired usage/procedure being performed. The below discussion of FIG. 1 will discuss medical procedure system 140 as one embodiment of the medical procedure systems 140 through 140-N.

Medical procedure system 140 receives, via one or more user interfaces, specification of patient specific factors, such as age, sex, body mass index (BMI), known medical/health condition, etc. that provide a range of patient specific information. Medical procedure system 140 also receives specification of a medical procedure to be performed. Based on the procedure and the patient specific information, medical procedure system may either recall a procedure and case-specific ML medical procedure model from a model store (e.g., a ML medical procedure model database) of medical procedure system 140, or request the procedure and case-specific ML medical procedure model from the ML medical procedure system 110.

In one embodiment, during a medical procedure (e.g., surgery, endoscopy, interventional radiology procedure, etc.), medical procedure system 140 ingests sensor data captured by one or more of the medical tools during a medical procedure. The sensor data can include, for example, stereoscopic imagery of a patient's anatomical structure(s), telemetry data indicative of speed, accelerations, rotation, direction, etc. of a robotic instrument, telemetry data of a non-robotic instrument (e.g., an instrument held and operated by a medical professional), etc. The medical procedure system 140 analyzes the received sensor data with the ML medical procedure model to, for example, track the progress of the medical procedure, identify actions performed during the medical procedure, match identified actions to steps of a predefined sequence of steps for a given medical procedure, dynamically update a sequence of steps of a medical procedure given case-specific and/or action-specific information.

In one embodiment, identification and tracking of steps of a medical procedure enable medical procedure system 140 to provide guidance and decision support to one or more medical professionals performing a medical procedure. This can include, for example, one or more of suggested next step(s) of a medical procedure, a graphical display of a next step, generation of reminders of critical information (e.g., "have you identified structure XYZ before the next incision"), a graphical display of critical information (e.g., a visual illustration of structure XYZ), notification when an action deviates from an expected step of a predefined sequence of steps, requests confirmation before enabling an action of a medical tool (e.g., detects an attempted deviation of a step or entry into a zone of a patient's anatomy, stops the medical tool, and requests confirmation before allowing the action to proceed), enforces "no-fly" zones that stop a medical tool from entering a specific zone of a patient's anatomy, warn of erratic action based on sensor data (e.g., speed, acceleration, periodicity of movement, direction and depth of movement, etc.), warn of erratic behaviour based on historical information (e.g., warn a surgeon who is acting in a way that is inconsistent with his or her own previous behaviour, such as detecting tremors due to fatigue, increased range of motion, etc.), as well as other actions to support an ongoing medical procedure. By providing this information to one or more medical professionals performing a medical procedure, medical procedure system 140 is able to provide guidance during the medical procedure, assist the medical professionals by preventing mistakes, help train medical professionals through the aforementioned guidance and assistance, etc.

In one embodiment, ML medical procedure server 110 is responsible for generating the ML medical procedure models utilized by medical procedure systems 140 through 140-N. In one embodiment, ML medical procedure server 110 trains procedure, case, and patient attribute-specific medical procedure models. The training can include performing a machine learning model based analysis on a plurality of sets of training data of prior medical procedures, where the training data can include visual information (e.g., digital images/mono or stereo video captured by a visual system of an endoscope to identify anatomical structures), sensor information (e.g., medical tool attributes, such as speed, depth of cuts, width of spreading, etc. relative to identified anatomical structures), steps and/or deviations from steps in a medical procedure, benchmarked information (e.g., sequence of steps with expected maximum and minimum times duration, tool usage, expected variations, etc.), patient-specific information (e.g., age, sex, BMI, relevant medical history, etc.), manual annotations of medical procedure data (e.g., annotations of important steps of anatomical structures in a procedure and/or step of a procedure), temporal annotations of the steps/phases of a medical procedure, as well as other relevant information.

ML medical procedure server 110 utilizes the training sets to generate an ML medical procedure model. In one embodiment, the medical procedure model includes multiple classifiers, such as a step identification classifier that is used to identify a current step in a medical procedure (e.g., current step is X, next step is Y with potential deviation of Z), an anatomy classifier that is used to identify one or more anatomical structures during a medical procedure based on input video or still image data (e.g., identification of a patient's arteries, organs, etc.), and one or more tool classifiers that identify proper and improper usage of a tool during a medical procedure based on medical tool sensor data (e.g., identification of an expected incision depth, tool movement(s) direction, speed, acceleration, etc.). In one embodiment, the training sets can include training sets with positive outcomes (e.g., where a surgical procedure was successful), as well as training sets with negative outcomes (e.g., errors in actual surgeries, suboptimal outcomes, complications, artificially performed mistakes in cadavers, etc.). In one embodiment, ML medical procedure server 110 periodically refines existing ML medical procedure models based on training sets having data captured during medical procedures performed by one or more of the medical procedure systems, newly created positive/negative training sets, etc. This continuous stream of new data from the medical procedure systems is used to periodically retrain and improve the classifiers of the ML medical procedure models.

In one embodiment, ML medical procedure server 110 sends trained medical procedure models, including the classifiers for each model, to the medical procedure systems 140 through 140-N. The models can be sent in response to requests from a medical procedure system, such as a request for a model for a specific procedure to be performed on a patient having specific characteristics, a request for all models for a specific procedure, a library of models for a range of medical procedures, etc. Furthermore, the ML medical procedure server 110 can provide updates to one or more previously provided ML medical procedure models based on the newly received training data. In one embodiment, the improved classifiers in the updated ML medical procedure models are pushed to one or more medical procedure systems periodically. As a result, the knowledge and experience of a potentially large group of medical professionals is collected, merged, and distilled into a knowledge base (e.g., the trained ML medical procedure models) that then benefits all medical professionals using the medical procedure systems by guiding and preventing errors during medical procedures.

Figure 2:
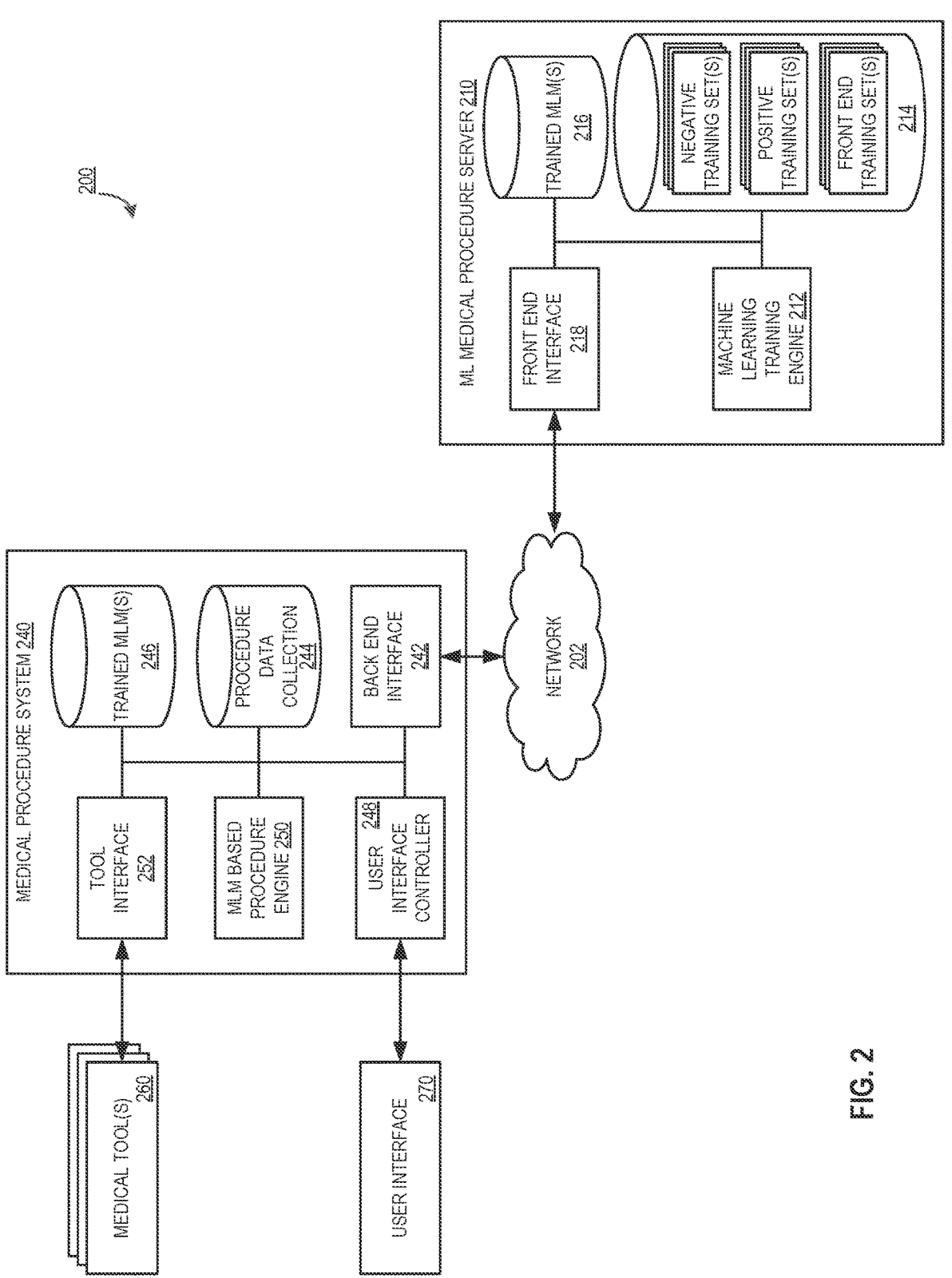
FIG. 2 is a block diagram of one embodiment of a medical procedure system and a machine learning model medical procedure server.

FIG. 2 is a block diagram of one embodiment 200 of a medical procedure system and a machine learning medical procedure server. Medical procedure system 240 and a ML medical procedure server 210 provide additional details for the medical procedure systems (e.g., 140 through 140-N) and the ML medical procedure server 110 discussed above in FIG. 1.

In one embodiment, the ML medical procedure server 210 includes a machine learning training engine 212, a data store 214 storing a plurality of sets of training data, a data store 216 of trained machine learning models (e.g., models and their respective classifiers), and a front end interface 218. In one embodiment, the medical procedure system 240 includes a back end interface 242, a data store of trained MLM(s) 246, an MLM based procedure engine 250, tool interface 252 to one or more medical tool(s) 260, and a user interface controller 248 coupled with user interface 270. In one embodiment, the medical procedure system 240 and an ML medical procedure server 210 communicate with each other over various networks 202 and network configurations as discussed above in FIG. 1.

The ML medical procedure server 210, in embodiments, can be implemented in a computing device, such as a server computer system, desktop computer, distributed computer systems, as well as other computing devices and configurations. In one embodiment, machine learning training engine 212 generates the trained MLM(s) maintained in data store 216. In embodiments, machine learning training engine 212 accesses the plurality of training sets (e.g., training data having positive outcomes, training data illustrating errors and/or negative outcomes, and front end training data captured by one or more medical procedure systems). Machine learning training engine 212 may utilize one or more machine learning techniques to train ML medical procedure model classifiers (e.g., the step identification classifier, anatomy classifier, and one or more tool classifiers discussed above in FIG. 1) for use during a medical procedure performed at medical procedure system 240. For example, machine learning training engine 212 may analyze the corpus of training set data in data store 214 utilizing hidden Markov models to generate step identification classifiers. As another example, machine learning training engine 212 may analyze the corpus of training set data in data store 214 utilizing deep neural networks to generate the step identification, anatomy, and tool classifiers. Other machine learning techniques can be utilized to generate the MLM classifiers discussed herein.

In one embodiment, once training is completed by machine learning training engine 212, ML medical procedure models including the trained classifiers are stored in data store 216. In one embodiment, data store 216 maintains a plurality of procedure and patient specific ML medical procedure models. For example, different ML medical procedure models can be maintained for each procedure for patients having different characteristics (e.g., age, gender, BMI, relevant medical history, etc.). However, the different ML medical procedure models need not be maintained for every combination of patient characteristic, as sets and/or ranges of characteristics can be associated with specific ML medical procedure models, and the ML medical procedure models can be configured with patient specific information. Furthermore, as discussed herein, the training performed by machine learning training engine 212 may be performed periodically to update and/or refine classifiers of the ML medical procedure models in data store 216 based on medical procedure data captured at one or more medical procedure systems (e.g., medical procedure system 240).

In one embodiment, front end interface 218 periodically communicates, in response to requests of medical procedure system 240 or in response to ML medical procedure model updates, one or more ML medical procedure models to medical procedure system 240 via back end interface 242. Medical procedure system 240 stores the received ML medical procedure models in trained MLM(s) data store 246 for use during a medical procedure.

In one embodiment, one or more medical professionals may interact with the medical procedure system 240 to perform a medical procedure using user interface 270 and medical tool(s) 260. User interface 270 can include one or more interfaces to medical procedure system 240, such as a graphical user interfaces, audio user interface, haptic feedback systems, virtual reality interfaces, user control mechanisms (e.g., joystick navigation), etc. One or more medical tool(s) 260 may be selectively coupled with medical procedure system 240 based on, for example a selected procedure, and can include minimally invasive medical tools (e.g., endoscopes, hypodermic injection tools, electrodes, etc.), robotically assisted tools (e.g., motorized tools that a medical professional can control via user interface 270), autonomous tools (e.g., medical tools that act without medical professional intervention based on instruction of a trained ML medical procedure model), as well as other types of medical tools 260.

User interface 270 enables a procedure to be selected and patient attributes to be entered that are relevant to the selected procedure. In another embodiment, the procedure and/or patient attributes can be automatically recognized using a ML medical procedure model (e.g., a selection model) that analyzes captured video or image data at the beginning of a medical procedure. Based on the procedure and patient attributes, MLM based procedure engine 250 selects an appropriate ML medical procedure model from trained MLM(s) data store 246. In one embodiment, the selected ML medical procedure model can be displayed to a medical professional via user interface 270 to enable the medical professional to accept or reject the model, as well as to configure a model with specific patient attributes, configure a model with procedural options, etc.

In one embodiment, during the medical procedure, MLM based procedure engine 250 utilizes the classifiers of the selected ML medical procedure model to identify steps in a procedure, identify anatomical structures of a patient undergoing the procedure, and/or identify appropriate medical tool usage 260. In one embodiment, the different identifications made by MLM based procedure engine 250 are based on received sensor input of the medical tools 260. For example, a stereoscopic endoscope can capture two or three dimensional medical imagery for analysis by MLM based procedure engine 250, to enable the MLM based procedure engine 250 to identify anatomical structures, identify steps in the procedure based on visibility of different parts of an anatomical structure, identify tools being used and whether they are appropriate at a given step, etc. from the captured image data. As another example, an accelerometer, gyroscope, pressure sensor, or other sensor attached to, for example, an incision device enables the MLM based procedure engine 250 to determine whether a medical professional is exceeding a recommended speed, exceeding a maximum cut depth, making a cut in the wrong direction, etc.

In one embodiment, based on the classifier analysis performed by MLM based procedure engine 250, MLM based procedure engine 250 may take one or more actions during a medical procedure. For example, MLM based procedure engine 250 can restrict or stop movement of a robotically assisted or autonomous medical tool based on an identified anatomical structure (e.g., enforce a "no-fly" zone where medical tools cannot go during a medical procedure or can only go if the surgeon overwrites a visual warning). As another example, MLM based procedure engine 250 can generate visual, audio, haptic, etc. warnings based on detected conditions (e.g., speed of tool use exceeding a maximum for given anatomical environment/proximity of specific structures, tool is moving in a direction towards a no-fly zone, deviation in expected next step of a procedure, etc.). As yet another example, MLM based procedure engine 250 can display one or more user interface elements that indicate to a medical professional a next step in a procedure, a visual of an expected view of anatomical structure, or other guidance. These controls, warnings, and guidance provided by MLM based procedure engine 250 provide guidance, decision support, and error prevention mechanisms to the medical professional(s) performing a medical procedure.

In one embodiment, in addition to tool interface 252 providing captured sensor data (e.g., telemetry, temperature, moisture, etc.) data captured by medical tools 260 during a medical procedure to MLM based procedure engine 250, tool interface 252 stores the data captured during the medical procedure in procedure data collection data store 244. The data store 244 is utilized to create sets of training data from actual medical procedures performed at medical procedure system 240. Then, back end interface 242 can periodically send the training set data in procedure data collection data store 244 to ML medical procedure server 210.

As discussed herein, ML medical procedure server 210 can collect training set data from a plurality of different medical procedure systems for a plurality of different procedures. As a result, the training of ML medical procedure model classifiers can be periodically refined based on the collected results of a group of medical professionals. This enables the classifiers of the ML medical procedure models to evolve into more precise classifiers capable of handling real world medical procedures for a wide array of types of procedures, types of variations in procedures, patients having different characteristics, etc. As a result, the error prevention and guidance offered by medical procedure system 240 operating in accordance with the discussion herein continues to improve over time.

FIG. 3 is a flowchart illustrating a process 300 for providing guidance and support with a medical procedure system, in accordance with an embodiment of the disclosure. The process is performed by processing logic that may comprise hardware (circuitry, dedicated logic, etc.), software (such as is run on a general purpose computer system or a dedicated machine), firmware, or a combination. In one embodiment, the process is performed by a medical procedure system (e.g., medical procedure system 140 or 240).

Referring to FIG. 3, processing logic begins by receiving an ML medical procedure model and stores the model in a data store (processing block 302). As discussed herein, the ML medical procedure model includes classifiers for identifying steps, anatomical structures, and tool operations in order to determine whether or not a stage of a medical procedure is being performed correctly and within certain predefined limits. In embodiments, the ML medical procedure model may be received in response to a request for a specific ML medical procedure model, in response to a request for a batch of ML medical procedure models, as a result of being periodically pushed to the medical procedure system, as an update to an existing ML medical procedure model, etc. The received ML medical procedure model is stored along with a plurality of models for a plurality of different medical procedures capable of being performed with the medical procedure system.

Processing logic receives specification of a medical procedure and patient characteristics (processing block 304). For example, a medical professional can enter a specific procedure (e.g., gallbladder removal) and one or more patient characteristics (e.g., age, sex, BMI, relevant medical conditions such as high blood pressure, etc.). Based on this received information, processing logic selects an ML medical procedure model from the data stored based on the specified medical procedure and configures the selected model based on the specified patient characteristics (processing block 306). Because the ML medical procedure model defines a series of steps of a medical procedure, the patient characteristics can customize the flow of the steps, as well as the steps themselves, so that they are appropriate for a given patient undergoing the medical procedure.

During the medical procedure, processing logic tracks an operation in the medical procedure using one or more sensors of a medical tool being used to perform the operation (processing block 308). In embodiments, the medical tools can include a plurality of different tools, such as control mechanisms (e.g., joystick, touch controls, a voice command controller, a VR controller, etc.), medical implements (e.g., endoscope, cutters, spreaders, clamps, etc.), as well as other tools. The sensors, such as accelerometers, gyroscopes, force sensors, etc. provide feedback to processing logic to inform processing logic as to how the operation in the procedure is being performed, so that processing logic can analyze the tracked operation using one or more classifiers of the ML medical procedure model to identify the step, anatomical structure, tool characteristics at the current operation (processing block 310). For example, the classifiers analyze the corpus of sensor data to determine when a tool is moving too fast, too slow, a cut is of an expected depth, a tool is moving in an unanticipated direction, etc. As another example, the classifiers analyze visual sensor data, such as endoscope data, to recognize anatomical structures in a field of view to determine if the expected anatomical structures are in view, recognize which medical tools are currently being used, whether a deviation in the medical procedure has occurred due to the view of unexpected anatomical structures, etc. Then, based on the results of the analysis, processing logic controls one or more processes of the medical procedure system during the medical procedure (processing block 312). In one embodiment, the process controls can include generating user interfaces that guide a medical professional through steps of the medical procedure, or provide communication with another medical professional to provide remote assistance during a medical procedure. Additionally, the process controls can include enforcing control mechanisms on the medical tools, such as overriding commands of the medical professional, stopping movement of a tool based on speed, direction, acceleration, taking an autonomous action, requesting acknowledgement before a deviation from an expected operation occurs, etc. Furthermore, alarms can be raised in response to deviations from one or more expected conditions of a ML medical procedure model, such as sending the alarm to another medical professional (e.g., a surgeon, nurse, or hospital management official if a resident is performing an operation).

Figure 6A:
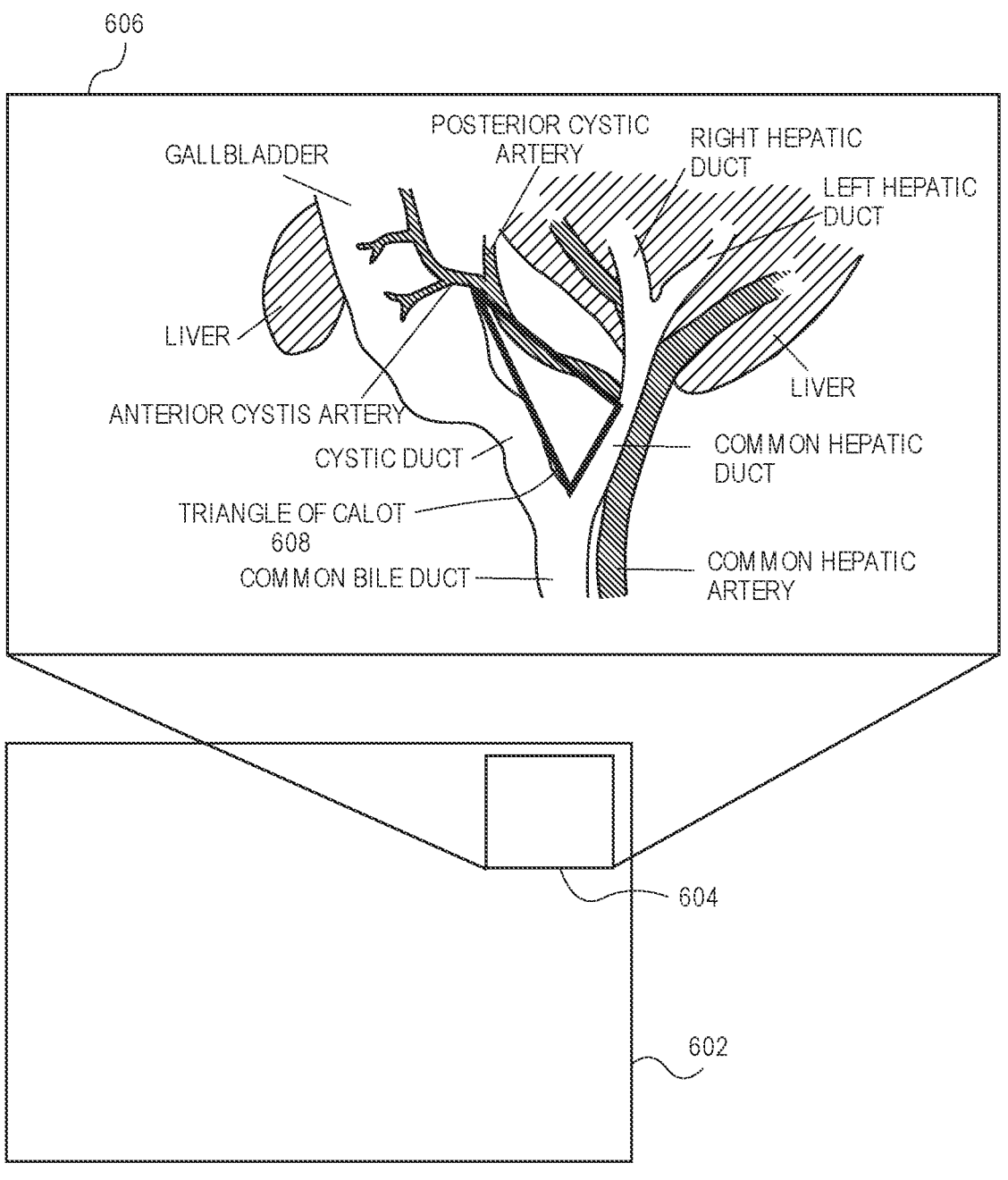
FIGS. 6A-6C illustrate exemplary user interfaces provided by a medical procedure system during an exemplary medical procedure.
Figures 6B, 6C:
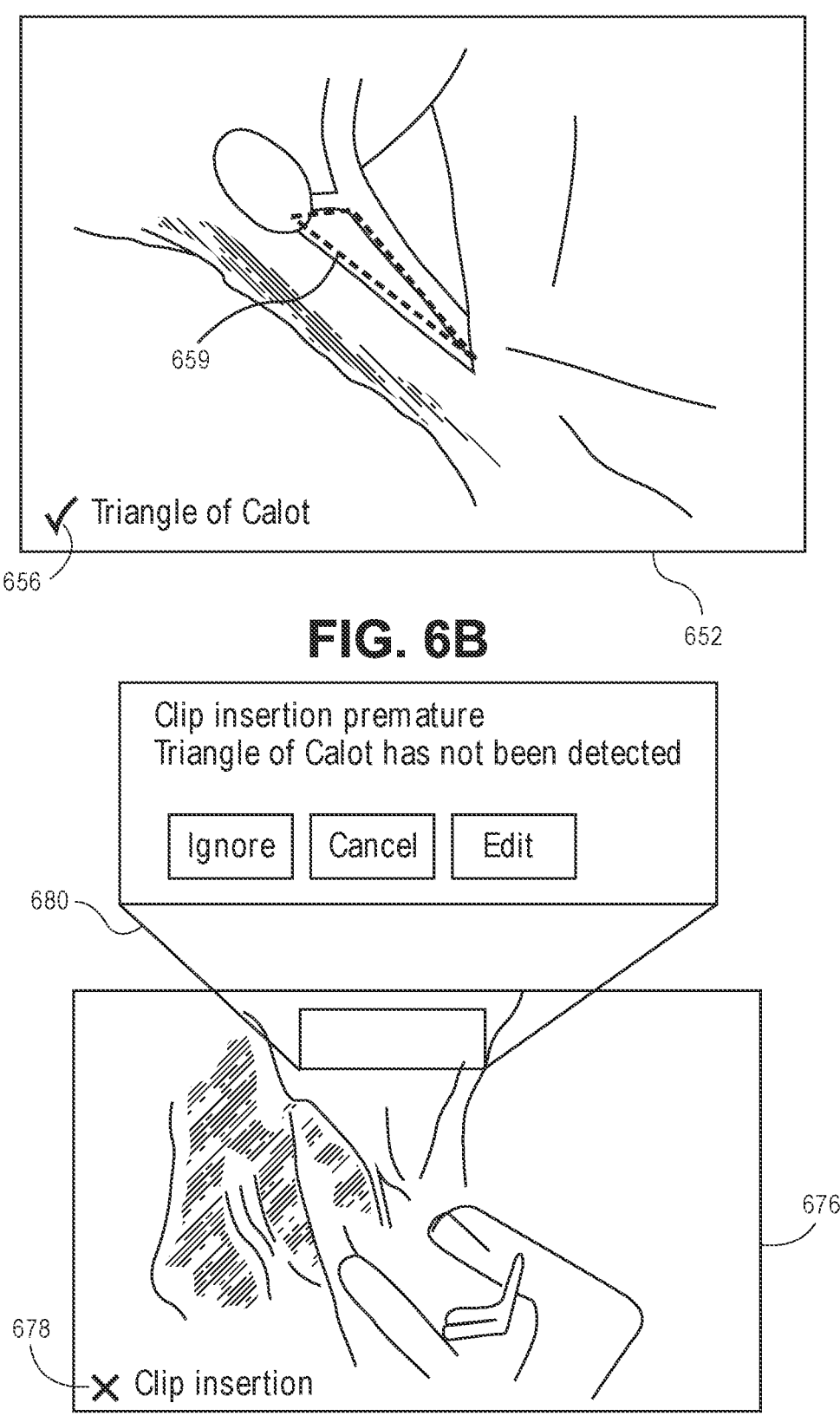

For example, FIG. 6A illustrates a graphical user interface 602, such a surgical console that can be used to display endoscope data captured during a medical procedure to the surgeon performing the procedure. When the current operation in the medical procedure is a dissection operation (e.g., as identified by the classifiers of the selected/configured ML medical procedure model), an insert 604 can be displayed 606 based on the current operation to inform the surgeon what anatomical structures should be within the surgeon's field of view at the completion of the dissection (e.g., the triangle of Calot 608 surrounded by other anatomical structures such as the liver, arteries, ducts, etc.). These anatomical structures, such as the highlighted triangle of Calot 608, can be significant waypoints during the proper procession of a medical procedure. FIG. 6B illustrates the same surgical console updated with a graphical user interface 652 that displays the recognized anatomical structure (e.g., triangle of Calot 656) which is highlighted 659 in the graphical user interface 652. This overlay on the field of view may be ephemeral to provide the surgeon with an indication that the preceding operation was performed successfully. However, as illustrated in FIG. 6C, when an operation does not occur in an expected order, such as detection of certain tools being used which are not expected, a graphical user interface 676 can be displayed that identifies the unrecognized element (e.g., a clip insertion 678). In one embodiment, processing logic controls the medical procedure in view of this unexpected event by generating a request for input 680. The input may enforce controls, such as preventing movement of a surgical robot, until the surgeon confirms via input 680 that the operation can proceed.

Returning to FIG. 3, processing logic then provides the tracked operations from the medical procedure to an ML medical server (processing block 314). As discussed herein, the tracked operations provide the ML medical server with training data sets of real medical procedure data, including sensor data, outcomes, deviations, annotations, etc. By providing the medical procedure data, front end training sets (e.g., training data sets in data store 214) can be expanded so that classifiers of corresponding ML medical procedure models can be retrained, refined, expanded for new circumstances (e.g., patient characteristics, complications during a medical procedure, as well as other circumstances), etc.

In embodiments, processing logic continually tracks operations and analyzes the tracked operations (e.g., processing blocks 308 and 310) to provide guidance and error protection in real time for the duration of the medical procedure. Furthermore, by continually tracking the medical procedure operations, processing logic is able to build a comprehensive set of data representing the medical procedure including visual data, medical tool sensory data, medical procedure step progression, approved deviations, etc. In one embodiment, this information may be annotated by a surgeon, or other medical professional, prior to providing the data to the ML medical server.

Figure 4:
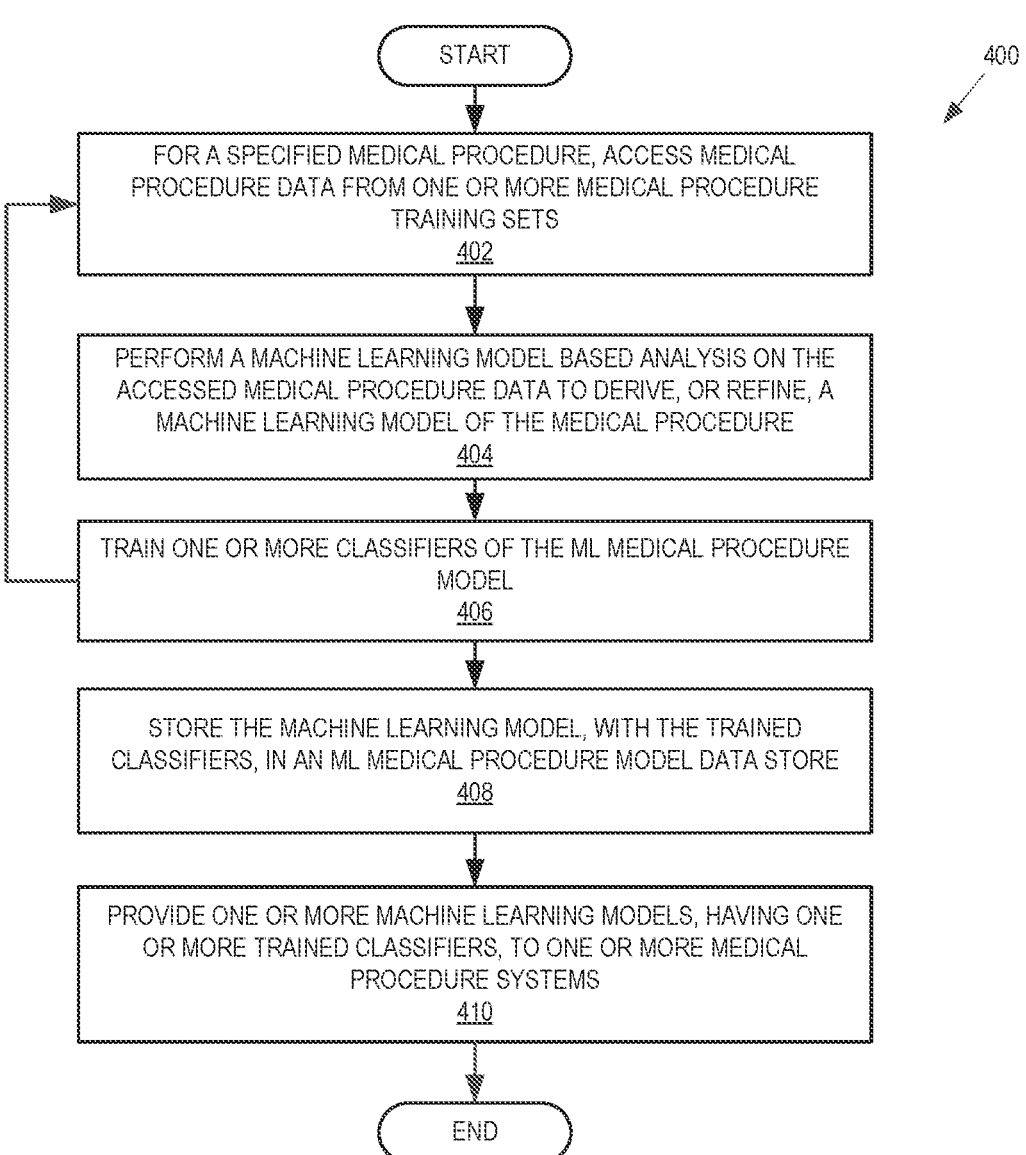
FIG. 4 is a flowchart illustrating a process for training a ML medical procedure model, in accordance with an embodiment of the disclosure.

FIG. 4 is a flowchart illustrating a process 400 for training an ML medical procedure model, in accordance with an embodiment of the disclosure. The process is performed by processing logic that may comprise hardware (circuitry, dedicated logic, etc.), software (such as is run on a general purpose computer system or a dedicated machine), firmware, or a combination. In one embodiment, the process is performed by a machine learning medical procedure server (e.g., ML medical procedure server 110 or 210).

Referring to FIG. 4, processing logic begins by accessing medical procedure data from one or more medical procedure training sets (processing block 402). In one embodiment, the medical procedure data is accessed based on a specified procedure. As discussed herein the medical procedure data can include a plurality of different types of data, such as medical tool sensor data (e.g., speed, direction, acceleration, pressure, moisture, etc.), visual data captured during a medical procedure (e.g., endoscope video or still image data), annotations made by a medical professional to the medical procedure data, etc. Furthermore, the training sets can include positive training data of successful procedures, negative training data that include mistakes (e.g., purposeful mistakes made during cadaver or animal surgery), as well as collected training data from procedures performed at different medical procedure systems.

Processing logic performs a machine learning model based analysis on the accessed medical procedure data to derive, or refine, a machine learning model of the medical procedure (processing block 404). Based on the analysis, processing logic trains one or more classifiers of the machine learning model for the medical procedure (processing block 406). As discussed herein, the machine learning model can include a plurality of classifiers that, once trained, enable the identification steps in a medical procedure, anatomical structures relevant to a given step in the medical procedure, and tool characteristics (e.g., speed of movement, direction of movement, depth of cut, amount of pressure applied, etc.). Processing logic can return to processing block 402 to analyze additional medical procedure data (e.g., positive, negative, and front end training sets of medical procedure data). Furthermore, new training sets of medical procedure data may be received which enable processing logic to return to processing block 402 to refine and/or expand the classifiers of the machine learning model.

Processing logic stores the machine learning model, with the trained classifiers, in a machine learning medical procedure model data store (processing block 408). Then, upon request from a medical procedure system, or during push operation initiated by processing logic, one or more machine learning models, having the trained classifiers, are provided to one or more medical procedure systems (processing block 410). As discussed herein, the machine learning models, when utilized by medical procedure systems, enable such systems to apply the machine learning models during medical procedures to control one or more operations of medical procedure systems (e.g., graphical user interface, medical tools, etc.) in order to prevent medical mistakes and guide medical professions performing various medical procedures.

Figure 5:
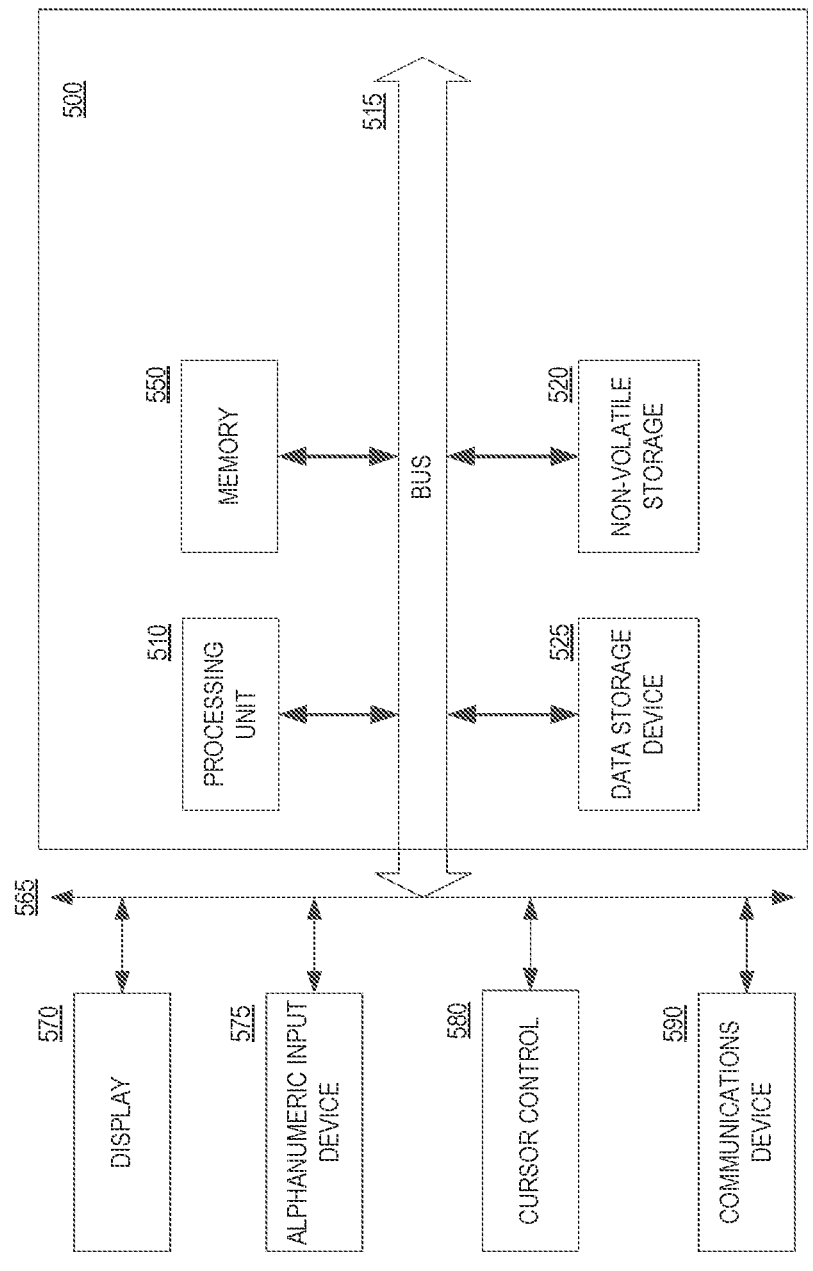
FIG. 5 is one embodiment of a computer system that may be used with the present invention.

FIG. 5 is one embodiment of a computer system that may be used with the present invention. It will be apparent to those of ordinary skill in the art, however, that other alternative systems of various system architectures may also be used.

The data processing system illustrated in FIG. 5 includes a bus or other internal communication means 515 for communicating information, and a processor 510 coupled to the bus 515 for processing information. The system further comprises a random access memory (RAM) or other volatile storage device 550 (referred to as memory), coupled to bus 515 for storing information and instructions to be executed by processor 510. Main memory 550 also may be used for storing temporary variables or other intermediate information during execution of instructions by processor 510. The system also comprises a read only memory (ROM) and/or static storage device 520 coupled to bus 515 for storing static information and instructions for processor 510, and a data storage device 525 such as a magnetic disk or optical disk and its corresponding disk drive. Data storage device 525 is coupled to bus 515 for storing information and instructions.

The system may further be coupled to a display device 570, such as a liquid crystal display (LCD), a light emitting diode (LED) display, etc. coupled to bus 515 through bus 565 for displaying information to a computer user. An alphanumeric input device 575, including alphanumeric and other keys, may also be coupled to bus 515 through bus 565 for communicating information and command selections to processor 510. An additional user input device is cursor control device 580, such as a mouse, a trackball, stylus, joystick, virtual reality controller, sensor feedback controller, or cursor direction keys coupled to bus 515 through bus 565 for communicating direction information and command selections to processor 510.

Another device, which may optionally be coupled to computer system 500, is a communication device 590 for accessing other nodes of a distributed system via a network. The communication device 590 may include any of a number of commercially available networking peripheral devices such as those used for coupling to an Ethernet, token ring, Internet, or wide area network. The communication device 590 may further be a null-modem connection, or any other mechanism that provides connectivity between the computer system 500 and the outside world. Note that any or all of the components of this system illustrated in FIG. 5 and associated hardware may be used in various embodiments of the present invention.

It will be appreciated by those of ordinary skill in the art that any configuration of the system may be used for various purposes according to the particular implementation. The control logic or software implementing the present invention can be stored in main memory 550, mass storage device 525, or other storage medium locally or remotely accessible to processor 510.

It will be apparent to those of ordinary skill in the art that the system, method, and process described herein can be implemented as software stored in main memory 550 or read only memory 520 and executed by processor 510. In embodiments, processor 510 may be a FPGA, CPU, GPU, or the like. This control logic or software may also be resident on an article of manufacture comprising a computer readable medium having computer readable program code embodied therein and being readable by the mass storage device 525 and for causing the processor 510 to operate in accordance with the methods and teachings herein.

The present invention may also be embodied in a handheld or portable device containing a subset of the computer hardware components described above. For example, the handheld device may be configured to contain only the bus 515, the processor 510, and memory 550 and/or 525. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 510, a data storage device 525, a bus 515, and memory 550, and only rudimentary communications mechanisms, such as a small touch-screen that permits the user to communicate in a basic manner with the device. In general, the more special-purpose the device is, the fewer of the elements need be present for the device to function.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described.

Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The invention claimed is:

1. A method for preventing surgical mistakes, the method comprising:
   controlling one or more operations of a medical procedure system during a medical procedure;
   wherein controlling the one or more operations of the medical procedure system comprises:
     determining at least one expected object expected to be visible during a current step of the corresponding medical procedure;
     providing an image of a field of view during the current step as input to a machine learning medical procedure model trained to identify objects; and
     in response to determining that the at least one expected object was not identified by the machine learning medical procedure model in the image of the field of view during the current step, preventing a movement of a medical tool coupled with the medical procedure system based on the current step and the determination that the at least one expected object is not visible.

2. The method of claim 1, wherein the at least one expected object includes at least one of an anatomical structure and a medical tool.

3. The method of claim 1, further comprising identifying the current step of the medical procedure.

4. The method of claim 3, wherein identifying the current step of the medical procedure includes identifying the current step of the medical procedure using one or more sensors of a medical tool.

5. The method of claim 1, wherein the machine learning medical procedure model is trained to identify at least one of anatomical structures and medical tools visible during the current step of the medical procedure.

6. The method of claim 1, wherein the medical procedure system analyzes the medical procedure using the machine learning medical procedure model in real time during the medical procedure.

7. The method of claim 1, wherein controlling the one or more operations of the medical procedure system comprises controlling motion of a medical tool coupled with the medical procedure system during the medical procedure.

8. The method of claim 7, wherein the medical tool comprises a robotically assisted medical device controlled by a medical professional performing the medical procedure.

9. The method of claim 1, wherein controlling the one or more operations of the medical procedure system comprises:
   preventing a requested motion of a medical tool based on one or more characteristics of the requested motion;
   generating a graphical user interface that requests an acknowledgement of a medical professional to allow the requested motion; and
   enabling the medical tool to move in accordance with the requested motion.

10. The method of claim 1, further comprising:
   tracking, by the medical procedure system, sensor data generated during the corresponding medical procedure from medical tool sensors coupled with the medical procedure system; and
   providing the tracked sensor data for generating or refining a machine learning medical procedure model.

11. A non-transitory computer-readable medium having computer-executable instructions stored thereon that, in response to execution by one or more processors of a medical procedure system, cause the medical procedure system to perform actions for preventing surgical mistakes, the actions comprising:
   controlling one or more operations of a medical procedure system during a medical procedure;
   wherein controlling the one or more operations of the medical procedure system comprises:
     determining at least one expected object expected to be visible during a current step of the corresponding medical procedure;
     providing an image of a field of view during the current step as input to a machine learning medical procedure model trained to identify objects; and
     in response to determining that the at least one expected object was not identified by the machine learning medical procedure model in the image of the field of view during the current step, preventing a movement of a medical tool coupled with the medical procedure system based on the current step and the determination that the at least one expected object is not visible.

12. The non-transitory computer-readable medium of claim 11, wherein the at least one expected object includes at least one of an anatomical structure and a medical tool.

13. The non-transitory computer-readable medium of claim 11, wherein the actions further comprise identifying the current step of the medical procedure.

14. The non-transitory computer-readable medium of claim 13, wherein identifying the current step of the medical procedure includes identifying the current step of the medical procedure using one or more sensors of a medical tool.

15. The non-transitory computer-readable medium of claim 11, wherein the machine learning medical procedure model is trained to identify at least one of anatomical structures and medical tools visible during the current step of the medical procedure.

16. The non-transitory computer-readable medium of claim 11, wherein the medical procedure system analyzes the medical procedure using the machine learning medical procedure model in real time during the medical procedure.

17. The non-transitory computer-readable medium of claim 11, wherein controlling the one or more operations of the medical procedure system comprises controlling motion of a medical tool coupled with the medical procedure system during the medical procedure.

18. The non-transitory computer-readable medium of claim 17, wherein the medical tool comprises a robotically assisted medical device controlled by a medical professional performing the medical procedure.

19. The non-transitory computer-readable medium of claim 11, wherein controlling the one or more operations of the medical procedure system comprises:

preventing a requested motion of a medical tool based on one or more characteristics of the requested motion;

generating a graphical user interface that requests an acknowledgement of a medical professional to allow the requested motion; and enabling the medical tool to move in accordance with the requested motion.

20. The non-transitory computer-readable medium of claim 11, wherein the actions further comprise:

tracking, by the medical procedure system, sensor data generated during the corresponding medical procedure from medical tool sensors coupled with the medical procedure system; and providing the tracked sensor data for generating or refining a machine learning medical procedure model.

* * * * *